(12) United States Patent
Elbe et al.

(10) Patent No.: US 7,388,097 B2
(45) Date of Patent: Jun. 17, 2008

(54) DIFLUOROMETHYL THIAZOLYL CARBOXANILIDES

(75) Inventors: Hans-Ludwig Elbe, Wuppertal (DE); Heiko Rieck, Foy-lés-Lyon (FR); Ralf Dunkel, Monheim (DE); Ulrike Wachendorff-Neumann, Neuwied (DE); Karl-Heinz Kuck, Langenfeld (DE); Astrid Mauler-Machnik, Leichlingen (DE); Martin Kugler, Leichlingen (DE); Thomas Jaetsch, Köln (DE); Peter Wachtler, Krefeld (DE)

(73) Assignee: Bayer CropScience AG, Monheim (DE)

( * ) Notice: Subject to any disclaimer, the term of this patent is extended or adjusted under 35 U.S.C. 154(b) by 573 days.

(21) Appl. No.: 10/502,994

(22) PCT Filed: Jan. 22, 2003

(86) PCT No.: PCT/EP03/00589

§ 371 (c)(1),
(2), (4) Date: Jan. 31, 2005

(87) PCT Pub. No.: WO03/066610

PCT Pub. Date: Aug. 14, 2003

(65) Prior Publication Data

US 2005/0124815 A1    Jun. 9, 2005

(30) Foreign Application Priority Data

Feb. 4, 2002    (DE) ............................... 102 04 391

(51) Int. Cl.
*C07D 285/02* (2006.01)
(52) U.S. Cl. ...................................... 548/136
(58) Field of Classification Search ........................ None
See application file for complete search history.

(56) References Cited

U.S. PATENT DOCUMENTS

| 4,837,242 | A |   | 6/1989 | Ohsumi et al. ............... 514/365 |
| 5,045,554 | A | * | 9/1991 | Alt et al. ...................... 514/365 |

FOREIGN PATENT DOCUMENTS

| EP | 0 545 099 |   | 6/1993 |
| JP | 9-132567 |   | 5/1997 |
| JP | 09132567 | * | 5/1997 |
| WO | 97/08148 |   | 3/1997 |

OTHER PUBLICATIONS

Bull. Korean Chem. Soc., vol. 21, (month unavailable) 2000, pp. 165-166, Nakcheol Jeong et al, "A Facile Preparation of the Fluoroaryl Zinc Halides: an Application to the Synthesis of Diflunisal".
Chem. Pharm. Bull, 40,(1), (month unavailable) 1992, pp. 240-244, Kiyoshi Taniguchi et al, "New 2-Aryliminoimidazolidines. II Synthesis and Antihypertensive Activity of 2-(Biphenylimino)-imidazolidines".
Patent Abstract of Japan vol 2002, No. 02, Apr. 2, 2002 & JP 2001 302605 A (Sumitomo Chem Co Ltd), Oct. 31, 2001.

* cited by examiner

*Primary Examiner*—Kamal A Saeed
(74) *Attorney, Agent, or Firm*—Richard E. L. Henderson

(57) ABSTRACT

The present invention relates to novel difluoromethylthiazolylcarboxanilides of the formula (I)

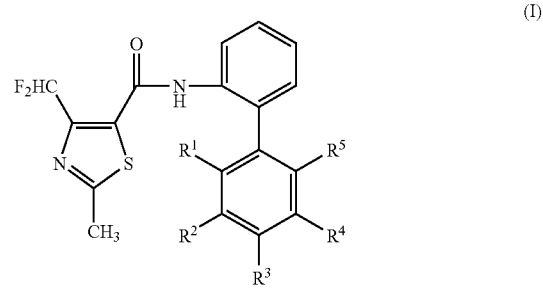

in which $R^1$, $R^2$, $R^3$, $R^4$ and $R^5$ are as defined in the disclosure, to a plurality of processes for preparing these substances and their use for controlling unwanted microorganisms, and to novel intermediates and their preparation.

13 Claims, No Drawings

DIFLUOROMETHYL THIAZOLYL CARBOXANILIDES

The present patent application has been filed under 35 U.S.C. 371 as a national stage application of PCT/EP03/00589, filed Jan. 22, 2003, which was published in German as International Patent Publication WO 03/066610 on Aug. 14, 2003, which is entitled to the right of priority of German Patent Application 102 04 391.4, filed Feb. 4, 2002.

The present invention relates to novel difluoromethylthiazolylcarboxanilides, to a plurality of processes for their preparation and to their use for controlling harmful microorganisms in crop protection and in the protection of materials.

It is already known that numerous carboxanilides have fungicidal properties (compare, for example, EP-A 0 545 099). The activity of the substances described therein is good; however, at low application rates it is sometimes unsatisfactory.

This invention now provides novel difluoromethylthiazolylcarboxanilides of the formula (I)

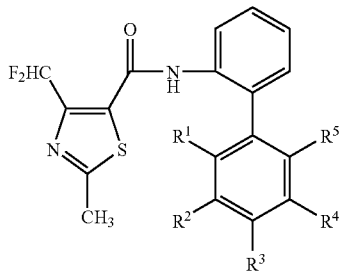

(I)

in which
$R^1$, $R^2$, $R^3$, $R^4$ and $R^5$ independently of one another represent hydrogen, halogen, cyano, nitro, $C_1$-$C_6$-alkyl, $C_2$-$C_6$-alkenyl, $C_1$-$C_4$-alkoxy, $C_1$-$C_4$-alkylthio, $C_1$-$C_4$-alkylsulphonyl, $C_3$-$C_6$-cycloalkyl, or represent $C_1$-$C_4$-haloalkyl, $C_1$-$C_4$-haloalkoxy, $C_1$-$C_4$-haloalkylthio or $C_1$-$C_4$-haloalkylsulphonyl having in each case 1 to 5 halogen atoms, with the proviso that $R^1$, $R^2$, $R^3$, $R^4$ and $R^5$ do not simultaneously represent hydrogen,
$R^1$ and $R^2$ or $R^2$ and $R^3$ furthermore together represent optionally halogen- or $C_1$-$C_6$-alkyl-substituted alkenylene.

Furthermore, it has been found that difluoromethylthiazolylcarboxanilides of the formula (I) are obtained when
a) difluoromethylthiazolylcarbonyl halides of the formula (II)

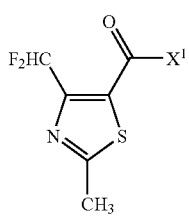

(II)

in which
$X^1$ represents halogen,
are reacted with aniline derivatives of the formula (III)

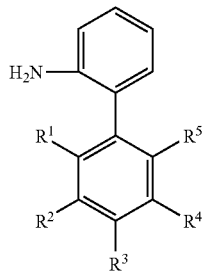

(III)

in which
$R^1$, $R^2$, $R^3$, $R^4$ and $R^5$ are as defined above,
if appropriate in the presence of an acid binder and if appropriate in the presence of a diluent, or
b) difluoromethylthiazolylcarboxhaloanilides of the formula (IV)

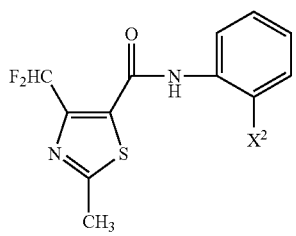

(IV)

in which
$X^2$ represents bromine or iodine,
are reacted with boronic acid derivatives of the formula (V)

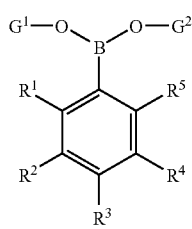

(V)

in which
$R^1$, $R^2$, $R^3$, $R^4$ and $R^5$ are as defined above,
$G^1$ and $G^2$ each represent hydrogen or together represent tetramethylethylene,
in the presence of a catalyst, if appropriate in the presence of an acid binder and if appropriate in the presence of a diluent, or
c) difluoromethylthiazolylcarboxanilide boronic acid derivatives of the formula (VI)

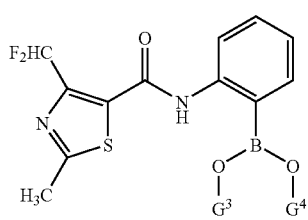

(VI)

in which

G³ and G⁴ each represent hydrogen or together represent tetramethylethylene, are reacted with halobenzene derivatives of the formula (VII)

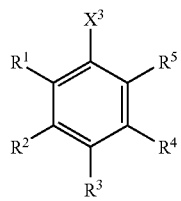

(VII)

in which $R^1$, $R^2$, $R^3$, $R^4$ and $R^5$ are as defined above, $X^3$ represents bromine, iodine or trifluoromethylsulphonyloxy, in the presence of a catalyst, if appropriate in the presence of an acid binder and if appropriate in the presence of a diluent.

Finally, it has been found that the novel difluoromethylthiazolylcarboxanilides of the formula (I) have very good microbicidal properties and can be used for controlling unwanted microorganisms both in crop protection and in the protection of materials.

Surprisingly, the difluoromethylthiazolylcarboxanilides of the formula (I) according to the invention have considerably better fungicidal activity than the constitutionally most similar active compounds of the prior art of the same direction of action.

The formula (I) provides a general definition of the difluoromethylthiazolylcarboxanilides according to the invention.

Preference is given to difluoromethylthiazolylcarboxanilides of the formula (I) in which $R^1$, $R^2$, $R^3$, $R^4$ and $R^5$ independently of one another represent hydrogen, fluorine, chlorine, bromine, cyano, nitro, methyl, ethyl, n- or i-propyl, n-, i-, s- or t-butyl, methoxy, ethoxy, methylthio, ethylthio, n- or i-propylthio, cyclopropyl, trifluoromethyl, trichloromethyl, trifluoroethyl, difluoromethoxy, trifluoromethoxy, difluorochloromethoxy, trifluoroethoxy, difluoromethylthio, difluorochloromethylthio or trifluoromethylthio, with the proviso that $R^1$, $R^2$, $R^3$, $R^4$ and $R^5$ do not simultaneously represent hydrogen, $R^1$ and $R^2$ or $R^2$ and $R^3$ furthermore together represent optionally fluorine-, chlorine-, bromine- or methyl-substituted butadienylene.

Particular preference is given to difluoromethylthiazolylcarboxanilides of the formula (I) in which $R^1$, $R^2$, $R^3$, $R^4$ and $R^5$ independently of one another represent hydrogen, fluorine, chlorine, bromine, methyl, methoxy, methylthio, trifluoromethyl, difluoromethoxy, trifluoromethoxy, difluoromethylthio or trifluoromethylthio, with the proviso that $R^1$, $R^2$, $R^3$, $R^4$ and $R^5$ do not simultaneously represent hydrogen.

Furthermore, very particular preference is given to difluoromethylthiazolylcarboxanilides of the formula (I) in which $R^1$, $R^2$, $R^4$ and $R^5$ each represent hydrogen and $R^3$ is as defined above.

Furthermore, very particular preference is given to difluoromethylthiazolylcarboxanilides of the formula (I) in which $R^1$, $R^2$, $R^4$ and $R^5$ each represent hydrogen and $R^3$ represents fluorine, chlorine, bromine, methyl, trifluoromethyl, trifluoromethoxy or trifluoromethylthio.

Furthermore, very particular preference is given to difluoromethylthiazolylcarboxanilides of the formula (I) in which $R^1$, $R^2$, $R^4$ and $R^5$ each represent hydrogen and $R^3$ represents cyano.

Furthermore, very particular preference is given to difluoromethylthiazolylcarboxanilides of the formula (I) in which $R^2$, $R^4$ and $R^5$ each represent hydrogen and $R^1$ and $R^3$ independently of one another are as defined above.

Furthermore, very particular preference is given to difluoromethylthiazolylcarboxanilides of the formula (I) in which $R^2$, $R^4$ and $R^5$ each represent hydrogen and $R^1$ and $R^3$ independently of one another represent fluorine, chlorine, bromine, methyl or trifluoromethyl.

Furthermore, very particular preference is given to difluoromethylthiazolylcarboxanilides of the formula (I) in which $R^1$, $R^4$ and $R^5$ each represent hydrogen and $R^2$ and $R^3$ independently of one another are as defined above.

Furthermore, very particular preference is given to difluoromethylthiazolylcarboxanilides of the formula (I) in which $R^1$, $R^4$ and $R^5$ each represent hydrogen and $R^2$ and $R^3$ independently of one another represent fluorine, chlorine, bromine, methyl or trifluoromethyl.

Furthermore, very particular preference is given to difluoromethylthiazolylcarboxanilides of the formula (I) in which $R^1$, $R^3$ and $R^5$ each represent hydrogen and $R^2$ and $R^4$ independently of one another are as defined above.

Furthermore, very particular preference is given to difluoromethylthiazolylcarboxanilides of the formula (I) in which $R^1$, $R^3$ and $R^5$ each represent hydrogen and $R^2$ and $R^4$ independently of one another represent fluorine, chlorine, bromine, methyl or trifluoromethyl.

Very particular preference is furthermore given to difluoromethylthiazolylcarboxanilides of the formula (I) in which $R^5$ represents hydrogen.

Using 2-methyl-4-(difluoromethyl)-1,3-thiazole-5-carbonylchloride and 3'-chloro-4'-fluoro-1,1'-biphenyl-2-amine as starting materials and a base, the course of the process a) according to the invention can be illustrated by the following equation:

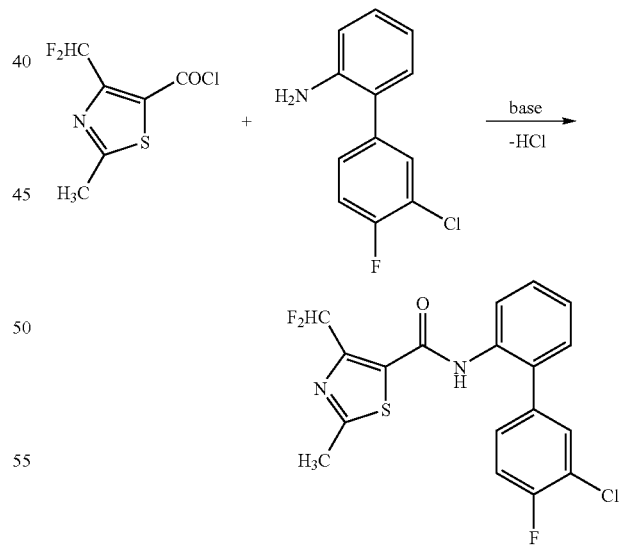

The formula (II) provides a general definition of the difluoromethylthiazolylcarbonyl halides required as starting materials for carrying out the process a) according to the invention. In this formula (II), $X^1$ preferably represents chlorine.

The difluoromethylthiazolylcarbonyl halides of the formula (II) are known and/or can be prepared by known processes (compare, for example, EP-A 0 276 177).

The formula (III) provides a general definition of the anilines furthermore required as starting materials for carrying out the process a) according to the invention. In this formula (III), $R^1$, $R^2$, $R^3$, $R^4$ and $R^5$ preferably and particularly preferably have those meanings which have already been mentioned in connection with the description of the compounds of the formula (I) according to the invention as being preferred and particularly preferred, respectively, for these radicals.

The aniline derivatives of the formula (III) are known and/or can be prepared by known methods (cf. for example Bull. Korean Chem. Soc. 2000, 21, 165-166; Chem. Pharm. Bull. 192, 40, 240-4; JP 09132567).

Using N-(2-iodophenyl)-2-methyl-4-(difluoromethyl)-1,3-thiazole-5-carboxamide and 3-chloro-4-fluorophenylboronic acid as starting materials and a catalyst and a base, the course of the process b) according to the invention can be illustrated by the following equation:

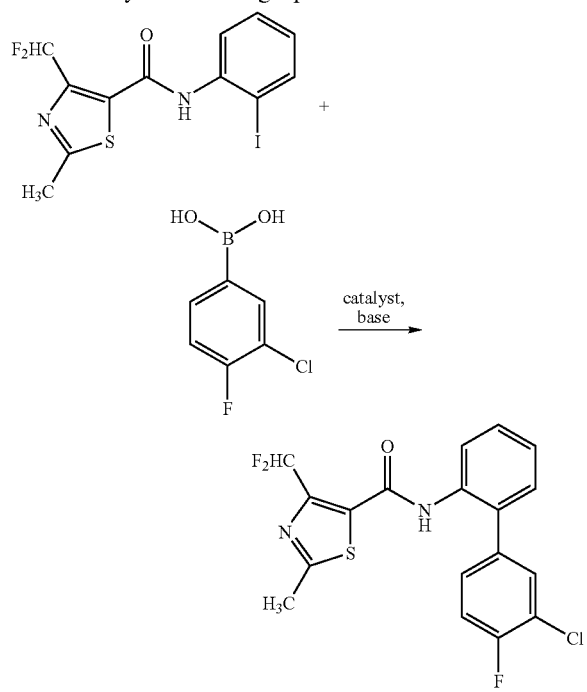

The formula (IV) provides a general definition of the difluoromethylthiazolylcarboxhaloanilides required as starting materials for carrying out the process b) according to the invention. In this formula (IV), $X^2$ preferably represents bromine or iodine.

The difluoromethylthiazolylcarboxhaloanilides of the formula (IV) have hitherto not been disclosed. They are novel chemical compounds and also form part of the subject-matter of the present application. They are obtained when d) difluoromethylthiazolylcarbonyl halides of the formula (II)

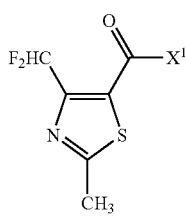

(II)

in which $X^1$ represents halogen, are reacted with 2-bromoaniline or 2-iodoaniline.

The difluoromethylthiazolylcarbonyl halides of the formula (II) required as starting materials for carrying out the process d) according to the invention have already been described further above in connection with the process a) according to the invention.

The substances 2-bromoaniline and 2-iodoaniline furthermore required as starting materials for carrying out the process d) according to the invention are known chemicals for synthesis.

The formula (V) provides a general definition of the boronic acid derivatives furthermore required as starting materials for carrying out the process b) according to the invention. In this formula (V), $R^1$, $R^2$, $R^3$, $R^4$ and $R^5$ preferably and particularly preferably have those meanings which have already been mentioned in connection with the description of the compounds of the formula (I) according to the invention as being preferred and particularly preferred, respectively, for these radicals. $G^1$ and $G^2$ preferably each represent hydrogen or together represent tetramethylethylene.

Boronic acid derivatives of the formula (V) are known chemicals for synthesis. They can also be prepared directly, immediately prior to the reaction, from halobenzene derivatives and boronic acid esters and be reacted further without work-up (see also the Preparation Examples).

Using 2-methyl-N-[2-(4,4,5,5-tetramethyl-1,3,2-dioxaborolan-2-yl)phenyl]-4-(difluoromethyl)-1,3-thiazole-5-carboxamide and 3-chloro-4-fluorophenyltrifluoromethanesulphonic acid as starting materials and a catalyst and a base, the course of the process c) according to the invention can be illustrated by the following equation:

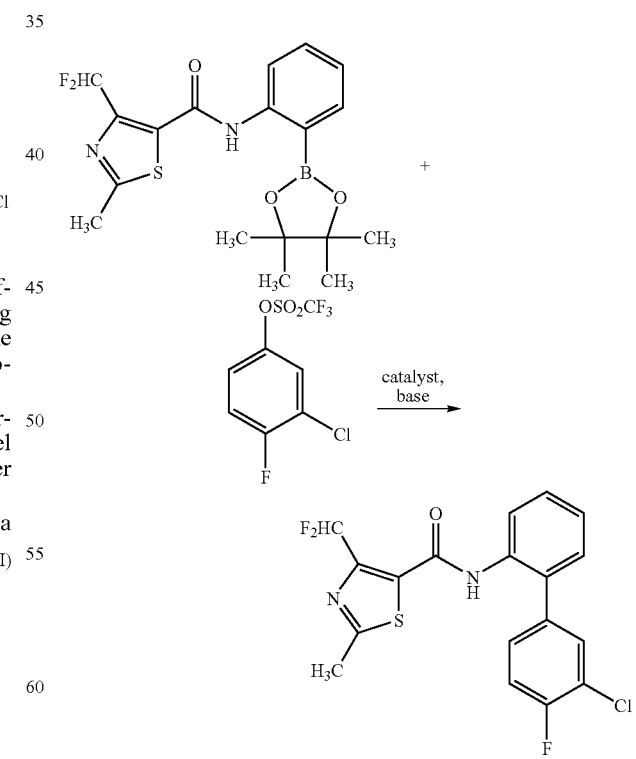

The formula (VI) provides a general definition of the difluoromethylthiazolylcarboxanilide boronic acid derivatives required as starting materials for carrying out the process c)

according to the invention. In this formula (VI), $G^3$ and $G^4$ preferably each represent hydrogen or together represent tetramethylethylene.

The difluoromethylthiazolylcarboxanilide boronic acid derivatives of the formula (VI) have hitherto not been disclosed. They are novel chemical compounds and also form part of the subject-matter of the present application. They are obtained when e) difluoromethylthiazolylcarbonyl halides of the formula (II)

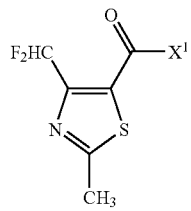

(II)

in which
$X^1$ represents halogen,
are reacted with aniline boronic acid derivatives of the formula (VIII).

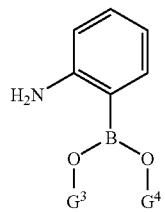

(VIII)

in which
$G^3$ and $G^4$ are as defined above,
if appropriate in the presence of an acid binder and if appropriate in the presence of a diluent.

The difluoromethylthiazolylcarbonyl halides of the formula (II) required as starting materials for carrying out the process e) according to the invention have already been described further above, in connection with process a) according to the invention.

The formula (VIII) provides a general definition of the aniline boronic acid derivatives furthermore required as starting materials for carrying out the process e) according to the invention. In this formula (VIII), $G^3$ and $G^4$ preferably each represent hydrogen or together represent tetramethylethylene.

The aniline boronic acid derivatives of the formula (VIII) required as starting materials for carrying out the process e) according to the invention are known chemicals for synthesis.

The formula (VII) provides a general definition of the halobenzene derivatives furthermore required as starting materials for carrying out the process c) according to the invention. In this formula (VII), $R^1$, $R^2$, $R^3$, $R^4$ and $R^5$ preferably and particularly preferably have those meanings which have already been mentioned in connection with the description of the compounds of the formula (I) according to the invention as being preferred and particularly preferred, respectively, for these radicals. $X^3$ preferably represents bromine, iodine or trifluoromethylsulphonyloxy.

Suitable diluents for carrying out the processes a), d) and e) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decaline; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl-t-butyl ether, methyl-t-amyl ether, dioxane, tetrahydrofuran, 1,2-dimethoxyethane, 1,2-diethoxyethane or anisole or amides, such as N,N-dimethylformamide, N,N-dimethylacetamide, N-methylformanilide, N-methylpyrrolidone or hexamethylphosphoric triamide.

The processes a), d) and e) according to the invention are, if appropriate, carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or caesium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the processes a), d) and e) according to the invention, the reaction temperatures can be varied within a relatively wide range. In general, the processes are carried out at temperatures of from 0° C. to 150° C., preferably at temperatures of from 20° C. to 110° C.

For carrying out the process a) according to the invention for preparing compounds of the formula (I), in general from 0.2 to 5 mol, preferably from 0.5 to 2 mol, of aniline derivative of the formula (III) are employed per mole of the difluoromethylthiazolylcarbonyl halide of the formula (II).

For carrying out the process d) according to the invention for preparing compounds of the formula (III), in general from 0.2 to 5 mol, preferably from 0.5 to 2 mol, of 2-bromoaniline or 2-iodoaniline are employed per mole of the difluoromethylthiazolylcarbonyl halide of the formula (II).

For carrying out the process e) according to the invention for preparing compounds of the formula (VI), in general from 0.2 to 5 mol, preferably from 0.5 to 2 mol, of aniline boronic acid derivative of the formula (VIII) are employed per mole of the difluoromethylthiazolylcarbonyl halide of the formula (II).

Suitable diluents for carrying out the processes b) and c) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decaline; ethers, such as diethyl ether, diisopropyl ether, methyl-t-butyl ether, methyl-t-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethylsulphoxide; sulphones, such as sulpholane; alcohols, such as methanol, ethanol, n- or i-propanol, n-, i-, sec- or tert-butanol, ethanediol, propane-1, 2-diol, ethoxyethanol, methoxyethanol, diethylene glycol monomethyl ether, diethylene glycol monoethyl ether, mixtures thereof with water or pure water.

When carrying out the processes b) and c) according to the invention, the reaction temperatures can be varied within a relatively wide range. In general, the processes are carried out at temperatures of from 0° C. to 150° C., preferably at temperatures of from 20° C. to 110° C.

The processes b) and c) according to the invention are, if appropriate, carried out in the presence of a suitable acid acceptor. Suitable acid acceptors are all customary inorganic or organic bases. These preferably include alkaline earth metal or alkali metal hydrides, hydroxides, amides, alkoxides, acetates, fluorides, phosphates, carbonates or bicarbonates, such as, for example, sodium hydride, sodium amide, lithium diisopropylamide, sodium methoxide, sodium ethoxide, potassium tert-butoxide, sodium hydroxide, potassium hydroxide, sodium acetate, sodium phosphate, potassium phosphate, potassium fluoride, caesium fluoride, sodium carbonate, potassium carbonate, potassium bicarbonate, sodium bicarbonate or caesium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

The processes b) and c) according to the invention are carried out in the presence of a catalyst, such as, for example, a palladium salt or complex. Suitable for this purpose are, preferably, palladium chloride, palladium acetate, tetrakis (triphenylphosphine)palladium, bis(triphenylphosphine)palladium dichloride or 1,1'-bis(diphenylphosphino)ferrocene palladium(II) chloride.

It is also possible to generate a palladium complex in the reaction mixture by separate addition of a palladium salt and a complex ligand, such as, for example, triethylphosphine, tri-tert-butylphosphine, tricyclohexylphosphine, 2-(dicyclohexylphosphine)biphenyl, 2-(di-tert-butylphosphine)biphenyl, 2-(dicyclohexylphosphine)-2'-(N,N-dimethylamino)biphenyl, triphenylphosphine, tris-(o-tolyl)phosphine, sodium 3-(diphenylphosphino)benzenesulphonate, tris-2-(methoxyphenyl)phosphine, 2,2'-bis(diphenylphosphine)-1,1'-binaphthyl, 1,4-bis-(diphenylphosphine)butane, 1,2-bis-(diphenylphosphine)ethane, 1,4-bis-(dicyclohexylphosphine)butane, 1,2-bis (dicyclohexylphosphine)ethane, 2-(dicyclohexylphosphine)-2'-(N,N-dimethylamino)biphenyl, bis(diphenylphosphino) ferrocene or tris-(2,4-tert-butylphenyl)phosphite to the reaction.

For carrying out the process b) according to the invention for preparing the compounds of the formula (I), in general from 1 to 15 mol, preferably from 2 to 8 mol, of boronic acid derivative of the formula (V) are employed per mole of the difluoromethylthiazolylcarboxhaloanilide of the formula (IV).

For carrying out the process c) according to the invention for preparing the compounds of the formula (I), in general from 1 to 15 mol, preferably from 2 to 8 mol, of halobenzene derivative of the formula (VII) are employed per mole of the difluoromethylthiazolylcarboxanilide boronic acid derivative of the formula (VI).

The processes a), b), c) and d) according to the invention are generally carried out under atmospheric pressure. However, it is also possible to operate under elevated or reduced pressure—in general between 0.1 bar and 10 bar.

The substances according to the invention have potent microbicidal activity and can be employed for controlling unwanted microorganisms, such as fungi and bacteria, in crop protection and in the protection of material.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

*Xanthomonas* species, such as, for example, *Xanthomonas campestris* pv. *oryzae;*

*Pseudomonas* species, such as, for example, *Pseudomonas syringae* pv. *lachrymans;*

*Erwinia* species, such as, for example, *Erwinia amylovora;*

*Pythium* species, such as, for example, *Pythium ultimum;*

*Phytophthora* species, such as, for example, *Phytophthora infestans;*

*Pseudoperonospora* species, such as, for example, *Pseudoperonospora humuli* or *Pseudoperonospora cubensis;*

*Plasmopara* species, such as, for example, *Plasmopara viticola;*

*Bremia* species, such as, for example, *Bremia lactucae;*

*Peronospora* species, such as, for example, *Peronospora pisi* or *P. brassicae;*

*Erysiphe* species, such as, for example, *Erysiphe graminis;*

*Sphaerotheca* species, such as, for example, *Sphaerotheca fuliginea;*

*Podosphaera* species, such as, for example, *Podosphaera leucotricha;*

*Venturia* species, such as, for example, *Venturia inaequalis;*

*Pyrenophora* species, such as, for example, *Pyrenophora teres* or *P. graminea* (conidia form: *Drechslera*, syn: *Helminthosporium*);

*Cochliobolus* species, such as, for example, *Cochliobolus sativus* (conidia form: *Drechslera*, syn: *Helminthosporium*);

*Uromyces* species, such as, for example, *Uromyces appendiculatus;*

*Puccinia* species, such as, for example, *Puccinia recondita;*

*Sclerotinia* species, such as, for example, *Sclerotinia sclerotiorum;*

*Tilletia* species, such as, for example, *Tilletia caries;*

*Ustilago* species, such as, for example, *Ustilago nuda* or *Ustilago avenae;*

*Pellicularia* species, such as, for example, *Pellicularia sasakii;*

*Pyricularia* species, such as, for example, *Pyricularia oryzae;*

*Fusarium* species, such as, for example, *Fusarium culmorum;*

*Botrytis* species, such as, for example, *Botrytis cinerea;*

*Septoria* species, such as, for example, *Septoria nodorum;*

*Leptosphaeria* species, such as, for example, *Leptosphaeria nodorum;*

*Cercospora* species, such as, for example, *Cercospora canescens;*

*Alternaria* species, such as, for example, *Alternaria brassicae*; and

*Pseudocercosporella* species, such as, for example, *Pseudocercosporella herpotrichoides.*

The active compounds according to the invention also have very good fortifying action in plants. Accordingly, they can be used for mobilizing the defences of the plant against attack by unwanted microorganisms.

In the present context, plant-fortifying (resistance-inducing) substances are to be understood as meaning those substances which are capable of stimulating the defence system of plants such that, when the treated plants are subsequently inoculated with unwanted microorganisms, they show substantial resistance against these microorganisms.

In the present case, unwanted microorganisms are to be understood as meaning phytopathogenic fungi, bacteria and viruses. Accordingly, the substances according to the invention can be used to protect plants for a certain period after the treatment against attack by the pathogens mentioned. The period for which protection is provided generally extends over 1 to 10 days, preferably 1 to 7 days, after the treatment of the plants with the active compounds.

The fact that the active compounds are well tolerated by plants at the concentrations required for controlling plant diseases permits the treatment of above-ground parts of plants, of propagation stock and seeds, and of the soil.

The active compounds according to the invention are also suitable for increasing the yield of crops. In addition, they show reduced toxicity and are well tolerated by plants.

At certain concentrations and application rates, the active compounds according to the invention can also be used as herbicides, for influencing plant growth and for controlling animal pests. They can also be used as intermediates and precursors for the synthesis of further active compounds.

The active compounds according to the invention can be used to treat all plants and parts of plants. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The treatment of the plants and the parts of plants with the active compounds according to the invention is carried out directly or by action on their surroundings, habitat or storage space, according to customary treatment methods, for example by dipping, spraying, evaporating, atomizing, broadcasting, spreading-on and, in the case of propagation material, in particular in the case of seeds, furthermore by one- or multi-layer coating.

In the protection of materials, the compounds according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (*Basidiomycetes*), and against slime organisms and algae.

Microorganisms of the following genera may be mentioned as examples:
*Alternaria*, such as *Alternaria tenuis*,
*Aspergillus*, such as *Aspergillus niger*,
*Chaetomium*, such as *Chaetomium globosum*,
*Coniophora*, such as *Coniophora puetana*,
*Lentinus*, such as *Lentinus tigrinus*,
*Penicillium*, such as *Penicillium glaucum*,
*Polyporus*, such as *Polyporus versicolor*,
*Aureobasidium*, such as *Aureobasidium pullulans*,
*Sclerophoma*, such as *Sclerophoma pityophila*,
*Trichoderma*, such as *Trichoderma viride*,
*Escherichia*, such as *Escherichia coli*,
*Pseudomonas*, such as *Pseudomonas aeruginosa*, and
*Staphylococcus*, such as *Staphylococcus aureus*.

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention can be used as such or in their formulations, also in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Examples of suitable mixing components are the following:

Fungicides:
aldimorph, ampropylfos, ampropylfos potassium, andoprim, anilazine, azaconazole, azoxystrobin,
benalaxyl, benodanil, benomyl, benzamacril, benzamacril-isobutyl, bialaphos, binapacryl, biphenyl, bitertanol, blasticidin-S, bromuconazole, bupirimate, buthiobate,
calcium polysulphide, carpropamide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram,
debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon,
edifenphos, epoxiconazole, etaconazole, ethirimol, etridiazole,
famoxadon, fenapanil, fenarimol, fenbuconazole, fenfuram, fenhexamide, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulphamide, flutolanil, flutriafol, folpet, fosetyl-aluminium, fosetylsodium, fthalide, fuberidazole, furalaxyl, furametpyr, furcarbonil, furconazole, furconazole-cis, furmecyclox,
guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, iprovalicarb, irumamycin, isoprothiolane, isovaledione,
kasugamycin, kresoxim-methyl, copper preparations, such as: copper hydroxide, copper naphthenate, copper oxychloride, copper sulphate, copper oxide, oxine-copper and Bordeaux mixture,
mancopper, mancozeb, maneb, meferimzone, mepanipyrim, mepronil, metalaxyl, metconazole, methasulphocarb, methfuroxam, metiram, metomeclam, metsulphovax, mildiomycin, myclobutanil, myclozolin,
nickel dimethyldithiocarbamate, nitrothal-isopropyl, nuarimol,
ofurace, oxadixyl, oxamocarb, oxolinic acid, oxycarboxim, oxyfenthiin,
paclobutrazole, pefurazoate, penconazole, pencycuron, phosdiphen, picoxystrobin, pimaricin, piperalin, polyoxin, polyoxorim, probenazole, prochloraz, procymidone, propamocarb, propanosine-sodium, propiconazole, propineb, pyraclostrobin, pyrazophos, pyrifenox, pyrimethanil, pyroquilon, pyroxyfur,
quinconazole, quintozene (PCNB), quinoxyfen,
sulphur and sulphur preparations, spiroxamines,
tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, trifloxystrobin, triflumizole, triforine, triticonazole,
uniconazole,
validamycin A, vinclozolin, viniconazole,
zarilamide, zineb, ziram and also
Dagger G, OK-8705, OK-8801,
α-(1,1-dimethylethyl)-β-(2-phenoxyethyl)-1H-1,2,4-triazole-1-ethanol,
α-(2,4-dichlorophenyl)-β-fluoro-β-propyl-1H-1,2,4-triazole-1-ethanol,
α-(2,4-dichlorophenyl)-β-methoxy-α-methyl-1H-1,2,4-triazole-1-ethanol,
α-(5-methyl-1,3-dioxan-5-yl)-β-[[4-(trifluoromethyl)-phenyl]-methylene]-1H-1,2,4-triazole-1-ethanol,
(5RS,6RS)-6-hydroxy-2,2,7,7-tetramethyl-5-(1H-1,2,4-triazol-1-yl)-3-octanone,
(E)-α-(methoxyimino)-N-methyl-2-phenoxy-phenylacetamide,
1-(2,4-dichlorophenyl)-2-(1H-1,2,4-triazol-1-yl)-ethanone O-(phenylmethyl)-oxime,
1-(2-methyl-1-naphthalenyl)-1H-pyrrole-2,5-dione,
1-(3,5-dichlorophenyl)-3-(2-propenyl)-2,5-pyrrolidinedione,
1-[(diiodomethyl)-sulphonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
1-[1-[2-[(2,4-dichlorophenyl)-methoxy]-phenyl]-ethenyl]-1H-imidazole,
1-methyl-5-nonyl-2-(phenylmethyl)-3-pyrrolidinole,
2',6'-dibromo-2-methyl-4'-trifluoromethoxy-4'-trifluoromethyl-1,3-thiazole-5-carboxanilide,
2,6-dichloro-5-(methylthio)-4-pyrimidinyl-thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)-sulphonyl]-5-(trichloromethyl)-1,3,4-thiadiazole,
2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrole-2,5-dione,
3,5-dichloro-N-[cyano[(1-methyl-2-propynyl)-oxy]-methyl]-benzamide, 3-(1,1-dimethylpropyl-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-hydroxyquinoline sulphate,
9H-xanthene-2-[(phenylamino)-carbonyl]-9-carboxylic hydrazide,
bis-(1-methylethyl)-3-methyl-4-[(3-methylbenzoyl)-oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholinehydrochloride,
ethyl[(4-chlorophenyl)-azo]-cyanoacetate,
potassium hydrogen carbonate,
methanetetrathiol sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidineamine,
N-(4-hexylphenyl)-1,4,5,6-tetrahydro-2-pyrimidineamine,
N-(5-chloro-2-methylphenyl)-2-methoxy-N-(2-oxo-3-oxazolidinyl)-acetamide,
N-(6-methoxy-3-pyridinyl)-cyclopropanecarboxamide,
N-[2,2,2-trichloro-1-[(chloroacetyl)-amino]-ethyl]-benzamide,
N-[3-chloro-4,5-bis-(2-propinyloxy)-phenyl]-N'-methoxy-methanimidamide,
N-formyl-N-hydroxy-DL-alanine-sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one,
4-[(3,4-dimethoxyphenyl)-3-(4-fluorophenyl)-acryloyl]-morpholine.

Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, acephate, acetamiprid, acrinathrin, alanycarb, aldicarb, aldoxycarb, alphacypermethrin, alphamethrin, amitraz, avermectin, AZ 60541, azadirachtin, azamethiphos, azinphos A, azinphos M, azocyclotin,
*Bacillus popilliae, Bacillus sphaericus, Bacillus subtilis, Bacillus thuringiensis,* baculoviruses, *Beauveria bassiana, Beauveria tenella,* bendiocarb, benfuracarb, bensultap, benzoximate, betacyfluthrin, bifenazate, bifenthrin, bioethanomethrin, biopermethrin, bistrifluron, BPMC, bromophos A, bufencarb, buprofezin, butathiofos, butocarboxim, butylpyridaben,
cadusafos, carbaryl, carbofuran, carbophenothion, carbosulphan, cartap, chloethocarb, chlorethoxyfos, chlorfenapyr, chlorfenvinphos, chlorfluazuron, chlormephos, chlorpyrifos, chlorpyrifos M, chlovaporthrin, chromafenozide, cis-resmethrin, cispermethrin, clocythrin, cloethocarb, clofentezine, clothianidine, cyanophos, cycloprene, cycloprothrin, cyfluthrin, cyhalothrin, cyhexatin, cypermethrin, cyromazine,
deltamethrin, demeton M, demeton S, demeton-S-methyl, diafenthiuron, diazinon, dichlorvos, dicofol, diflubenzuron, dimethoat, dimethylvinphos, diofenolan, disulphoton, docusat-sodium, dofenapyn,
eflusilanate, emamectin, empenthrin, endosulphan, *Entomopfthora* spp., esfenvalerate, ethiofencarb, ethion, ethoprophos, etofenprox, etoxazole, etrimfos,
fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazuron, flubrocythrinate, flucycloxuron, flucythrinate, flufenoxuron, flumethrin, flutenzine, fluvalinate, fonophos, fosmethilan, fosthiazate, fubfenprox, furathiocarb,
granulosis viruses,
halofenozide, HCH, heptenophos, hexaflumuron, hexythiazox, hydroprene,
imidacloprid, indoxacarb, isazofos, isofenphos, isoxathion, ivermectin,
nuclear polyhedrosis viruses,
lambda-cyhalothrin, lufenuron,
malathion, mecarbam, metaldehyde, methamidophos, *Metharhizium anisopliae, Metharhizium flavoviride,* methidathion, methiocarb, methoprene, methomyl, methoxyfenozide, metolcarb, metoxadiazone, mevinphos, milbemectin, milbemycin, monocrotophos,
naled, nitenpyram, nithiazine, novaluron,
omethoate, oxamyl, oxydemethon M,
*Paecilomyces fumosoroseus,* parathion A, parathion M, permethrin, phenthoate, phorat, phosalone, phosmet, phosphamidon, phoxim, pirimicarb, pirimiphos A, pirimiphos M, profenofos, promecarb, propargite, propoxur, prothiofos, prothoat, pymetrozine, pyraclofos, pyresmethrin, pyrethrum, pyridaben, pyridathion, pyrimidifen, pyriproxyfen,
quinalphos, ribavirin,
salithion, sebufos, silafluofen, spinosad, spirodiclofen, sulphotep, sulprofos,
tau-fluvalinate, tebufenozide, tebufenpyrad, tebupirimiphos, teflubenzuron, tefluthrin, temephos, temivinphos, terbufos, tetrachlorvinphos, tetradifon thetacypermethrin, thiacloprid, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb,
vamidothion, vaniliprole, *Verticillium lecanii,*
YI 5302, Zeta-cypermethrin, Zolaprofos
(1R-cis)-[5-(phenylmethyl)-3-furanyl]-methyl-3-[(dihydro-2-oxo-3(2H)furanylidene)-methyl]-2,2-dimethylcyclopropanecarboxylate,
(3-phenoxyphenyl)-methyl-2,2,3,3-tetramethylcyclopropanecarboxylate,
1-[(2-chloro-5-thiazolyl)methyl]tetrahydro-3,5-dimethyl-N-nitro-1,3,5-triazine-2(1H)-imine,
2-(2-chloro-6-fluorophenyl)-4-[4-(1,1-dimethylethyl)phenyl]-4,5-dihydro-oxazole,
2-(acetyloxy)-3-dodecyl-1,4-naphthalenedione,
2-chloro-N-[[[4-(1-phenylethoxy)-phenyl]-amino]-carbonyl]-benzamide,
2-chloro-N-[[[4-(2,2-dichloro-1,1-difluoroethoxy)-phenyl]-amino]-carbonyl]-benzamide,
3-methylphenyl propylcarbamate,
4-[4-(4-ethoxyphenyl)-4-methylpentyl]-1-fluoro-2-phenoxy-benzene,
4-chloro-2-(1,1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)pyridazinone,
4-chloro-5-[(6-chloro-3-pyridinyl)methoxy]-2-(3,4-dichlorophenyl)-3 (2H)pyridazinone,
*Bacillus thuringiensis* strain EG-2348,
[2-benzoyl-1-(1,1-dimethylethyl)-hydrazinobenzoic acid,
2,2-dimethyl-3-(2,4-dichlorophenyl)-2-oxo-1-oxaspiro[4.5]dec-3-en-4-yl butanoate,
[3-[(6-chloro-3-pyridinyl)methyl]-2-thiazolidinylidene]-cyanamide,
dihydro-2-(nitromethylene)-2H-1,3-thiazine-3(4H)-carboxaldehyde,
ethyl[2-[[1,6-dihydro-6-oxo-1-(phenylmethyl)-4-pyridazinyl]oxy]ethyl]-carbamate,
N-(3,4,4-trifluoro-1-oxo-3-butenyl)-glycine,
N-(4-chlorophenyl)-3-[4-(difluoromethoxy)phenyl]-4,5-dihydro-4-phenyl-1H-pyrazole-1-carboxamide,
N-[(2-chloro-5-thiazolyl)methyl]-N'-methyl-N''-nitroguanidine,
N-methyl-N'-(1-methyl-2-propenyl)-1,2-hydrazinedicarbothioamide,
N-methyl-N'-2-propenyl-1,2-hydrazinedicarbothioamide,
O,O-diethyl [2-(dipropylamino)-2-oxoethyl]-ethylphosphoramidothioate,
N-cyanomethyl-4-trifluoromethyl-nicotinamide,
3,5-dichloro-1-(3,3-dichloro-2-propenyloxy)-4-[3-(5-trifluoromethylpyridine-2-yloxy)-propoxy]-benzene.

A mixture with other known active compounds, such as herbicides, or with fertilizers and growth regulators, is also possible.

In addition, the compounds of the formula (I) according to the invention also have very good antimycotic activity. They have a very broad antimycotic activity spectrum in particular against dermatophytes and yeasts, moulds and diphasic fungi, (for example against *Candida* species, such as *Candida albicans, Candida glabrata*), and *Epidermophyton floccosum, Aspergillus* species, such as *Aspergillus niger* and *Aspergillus fumigatus, Trichophyton* species, such as *Trichophyton mentagrophytes, Microsporon* species such as *Microsporon canis* and *audouinii*. The list of these fungi by no means limits the mycotic spectrum covered, but is only for illustration.

The active compounds can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low volume method, or to inject the active compound preparation or the active compound itself into the soil. It is also possible to treat the seeds of the plants.

When using the active compounds according to the invention as fungicides, the application rates can be varied within a relatively wide range, depending on the kind of application. For the treatment of parts of plants, the active compound application rates are generally between 0.1 and 10,000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10,000 g/ha, preferably between 1 and 5000 g/ha.

As already mentioned above, it is possible to treat all plants and their parts with active compounds according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetical engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having new properties ("traits") and which have been obtained by conventional breeding, by mutagenesis or by recombinant DNA techniques. They can be cultivars, varieties, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasized are in particular increased defence of the plants against insects by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are also particularly emphasized are the increased defence of the plants to fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucoton® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the compounds of the formula (I) or the active compound mixtures according to the invnetion. The preferred ranges stated above for the active compounds and mixtures also apply to the treatment of these plants. Particular emphasis is given to the treatment of plants with the compounds or mixtures specifically mentioned in the present text.

PREPARATION EXAMPLES

Example 1

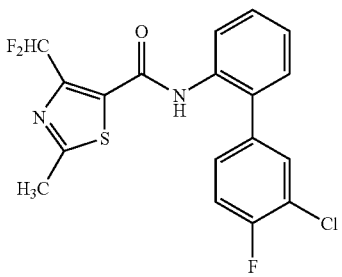

Process a)

0.288 g (1.3 mmol) of 3'-chloro-4'-fluoro-1,1'-biphenyl-2-amine and 0.33 g (1.5 mmol) of 2-methyl-4-(difluoromethyl)-1,3-thiazole-5-carbonyl chloride are dissolved in 6 ml of tetrahydrofuran, and 0.36 ml (2.6 mmol) of triethylamine is added. The reaction solution is stirred at 60° C. for 16 h. For work-up, the mixture is concentrated and the residue is chromatographed on silica gel using cyclohexane/ethyl acetate.

This gives 0.434 g (84% of theory) of N-(3'-chloro-4'-fluoro-1,1'-biphenyl-2-yl)-2-methyl-4-(difluoromethyl)-1,3-thiazole-5-carboxamide of logP (pH 2.3)=3.28.

The compounds of the formula (I) listed in Table 1 below are obtained analogously to Example 1 and in accordance with the statements in the general descriptions of the processes a) and b).

(I)

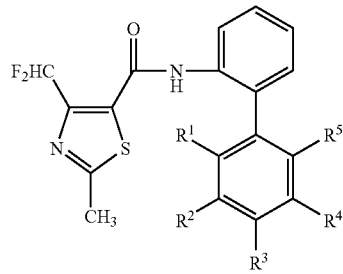

TABLE 1

| Ex. | $R^1$ | $R^2$ | $R^3$ | $R^4$ | $R^5$ | logP |
|-----|-----|-----|-----|-----|-----|------|
| 2 | H | H | Br | H | H | 3.47 |
| 3 | H | H | $CF_3$ | H | H | 3.52 |
| 4 | H | Cl | H | H | H | 3.37 |
| 5 | H | H | $OCF_3$ | H | H | 3.72 |
| 6 | H | H | $SCH_3$ | H | H | 3.39 |
| 7 | H | H | F | H | H | 3.09 |
| 8 | H | Cl | Cl | H | H | 3.58 |
| 9 | Cl | H | Cl | H | H | 3.58 |
| 10 | $CH_3$ | H | Cl | H | H | 3.77 |
| 11 | H | F | Cl | H | H | 3.29 |
| 12 | H | Cl | $CH_3$ | H | H | 3.62 |
| 13 | F | H | Cl | H | H | 3.26 |
| 14 | H | F | H | Cl | H | 3.36 |
| 15 | F | H | Br | H | H | 3.34 |
| 16 | H | $CH_3$ | Cl | H | H | 3.66 |
| 17 | H | Cl | H | Cl | H | 3.7 |
| 18 | H | F | H | F | H | 3.07 |
| 19 | H | $CF_3$ | Cl | H | H | 3.66 |
| 20 | H | F | F | H | H | 3.04 |
| 21 | H | H | Cl | H | H | 3.27 |
| 22 | H | F | Br | H | H | 3.36 |
| 23 | H | F | $CF_3$ | H | H | 3.43 |
| 24 | F | H | F | H | H | 2.93 |
| 25 | H | H | CN | H | H | 2.51 |
| 26 | H | H | H | H | H | 3.50 |

Preparation of an Intermediate of the Formula (III)

Example (III-1)

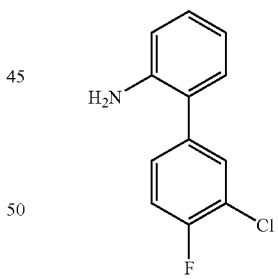

Under argon, 38.8 g (223 mmol) of 3-chloro-4-fluorophenylboronic acid and 40.6 g (186 mmol) of 2-iodoaniline are dissolved in 220 ml of toluene, 22 ml of ethanol and 45 ml of a 4 M solution of sodium bicarbonate. 4.3 g (4 mmol) of tetrakis(triphenylphosphine)palladium(0) are added, and the reaction solution is then stirred at 80° C. and under argon for 16 hours. The organic phase is separated off, dried over magnesium sulphate and concentrated. The residue is chromatographed on silica gel using cyclohexane/ethyl acetate.

This gives 22.5 g (48% of theory) of 3'-chloro-4'-fluoro-1,1'-biphenyl-2-amine (purity 88%) of logP (pH 2.3)=3.01.

The determination of the logP values given in the tables and Preparation Examples above is carried out in accordance with EEC Directive 79/831 Annex V.A8 by HPLC (High Performance Liquid Chromatography) on a reverse-phase column (C 18). Temperature: 43° C.

The determination is carried out in the acidic range at pH 2.3 using the mobile phases 0.1% aqueous phosphoric acid and acetonitrile; linear gradient from 10% acetonitrile to 90% acetonitrile.

Calibration is carried out using unbranched alkan-2-ones (of 3 to 16 carbon atoms) with known logP values (determination of the logP values by the retention times using linear interpolation between two successive alkanones).

The lambda max values were determined in the maxima of the chromatographic signals using the UV spectra from 200 nm to 400 nm.

USE EXAMPLES
Example A

*Venturia* Test (Apple)/Protective

| Solvents: | 24.5 parts by weight of acetone |
| | 24.5 parts by weight of dimethylacetamide |
| Emulsifier: | 1.0 part by weight of alkylaryl polyglycol ether |

To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the apple scab pathogen *Venturia inaequalis* and then remain in an incubation cabin at about 20° C. and 100% relative atmospheric humidity for 1 day.

The plants are then placed in a greenhouse at about 21° C. and a relative atmospheric humidity of about 90%.

Evaluation is carried out 10 days after the inoculation. 0% means an efficacy which corresponds to that of the control, whereas an efficacy of 100% means that no infection is observed.

TABLE A

Venturia Test (Apple)/protective

| Ex. | Active compound | Application rate of active compound in g/ha | % efficacy |
|---|---|---|---|
| According to EP-A 0 545 099: | | | |
| 3.37 | (structure: thiazole with $F_3C$, $CH_3$, amide-NH, biphenyl with F) | 10 | 32 |
| According to the invention: | | | |
| 2 | (structure: thiazole with $F_2HC$, $CH_3$, amide-NH, biphenyl with Br) | 10 | 100 |
| 3 | (structure: thiazole with $F_2HC$, $CH_3$, amide-NH, biphenyl with $CF_3$) | 10 | 100 |

TABLE A-continued

Venturia Test (Apple)/protective

| Ex. | Active compound | Application rate of active compound in g/ha | % efficacy |
| --- | --- | --- | --- |
| 4 | F₂HC-thiazole(2-CH₃)-C(=O)NH-(2-(3-chlorophenyl)phenyl) | 10 | 100 |
| 5 | F₂HC-thiazole(2-CH₃)-C(=O)NH-(2-(4-OCF₃-phenyl)phenyl) | 10 | 87 |
| 6 | F₂HC-thiazole(2-CH₃)-C(=O)NH-(2-(4-SCH₃-phenyl)phenyl) | 10 | 99 |
| 7 | F₂HC-thiazole(2-CH₃)-C(=O)NH-(2-(4-fluorophenyl)phenyl) | 10 | 100 |
| 9 | F₂HC-thiazole(2-CH₃)-C(=O)NH-(2-(2,4-dichlorophenyl)phenyl) | 10 | 98 |

TABLE A-continued

Venturia Test (Apple)/protective

| Ex. | Active compound | Application rate of active compound in g/ha | % efficacy |
|---|---|---|---|
| 10 | 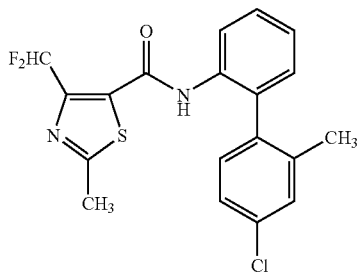 | 10 | 100 |
| 11 | 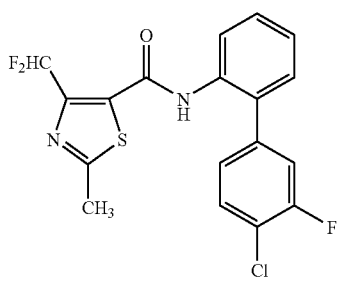 | 10 | 100 |
| 12 | 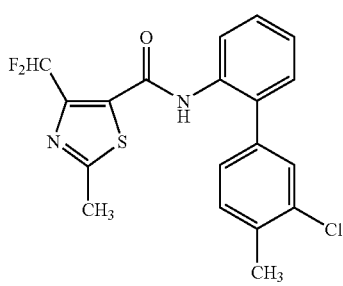 | 10 | 100 |

Example B

*Botrytis* Test (Bean)/Protective

| | |
|---|---|
| Solvents: | 24.5 parts by weight of acetone |
| | 24.5 parts by weight of dimethylacetamide |
| Emulsifier: | 1.0 part by weight of alkylaryl polyglycol ether |

To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, 2 small pieces of agar colonized by *Botrytis cinerea* are placed onto each leaf. The inoculated plants are placed in a dark chamber at about 20° C. and 100% relative atmospheric humidity.

2 days after the inoculation, the size of the infected areas on the leaves is evaluated. 0% means an efficacy which corresponds to that of the control, whereas an efficacy of 100% means that no infection is observed.

TABLE B

Botrytis Test (Bean)/protective

| Ex. | Active compound | Application rate of active compound in g/ha | % efficacy |
|---|---|---|---|
| According to EP-A 0 545 099: | | | |
| 3.37 | F$_2$HC-thiazole(CH$_3$)-C(O)NH-biphenyl-4'-F | 100 | 90 |
| According to the invention: | | | |
| 2 | F$_2$HC-thiazole(CH$_3$)-C(O)NH-biphenyl-4'-Br | 100 | 100 |
| 3 | F$_2$HC-thiazole(CH$_3$)-C(O)NH-biphenyl-4'-CF$_3$ | 100 | 100 |
| 4 | F$_2$HC-thiazole(CH$_3$)-C(O)NH-biphenyl-3'-Cl | 100 | 100 |
| 5 | F$_2$HC-thiazole(CH$_3$)-C(O)NH-biphenyl-4'-OCF$_3$ | 100 | 79 |

TABLE B-continued

Botrytis Test (Bean)/protective

| Ex. | Active compound | Application rate of active compound in g/ha | % efficacy |
|---|---|---|---|
| 6 | (2-methyl-4-difluoromethyl-thiazol-5-yl)-carboxamide of 4'-(methylthio)biphenyl-2-amine | 100 | 94 |
| 7 | (2-methyl-4-difluoromethyl-thiazol-5-yl)-carboxamide of 4'-fluorobiphenyl-2-amine | 100 | 94 |
| 9 | (2-methyl-4-difluoromethyl-thiazol-5-yl)-carboxamide of 2',4'-dichlorobiphenyl-2-amine | 100 | 95 |
| 10 | (2-methyl-4-difluoromethyl-thiazol-5-yl)-carboxamide of 4'-chloro-2'-methylbiphenyl-2-amine | 100 | 100 |
| 11 | (2-methyl-4-difluoromethyl-thiazol-5-yl)-carboxamide of 4'-chloro-3'-fluorobiphenyl-2-amine | 100 | 100 |

TABLE B-continued

Botrytis Test (Bean)/protective

| Ex. | Active compound | Application rate of active compound in g/ha | % efficacy |
|---|---|---|---|
| 12 | F$_2$HC-thiazole(CH$_3$)-C(O)NH-phenyl-(3-Cl,4-CH$_3$-phenyl) | 100 | 100 |

Example C

In Vitro Test for the ED$_{50}$ Determination of Microorganisms

A methanolic solution of the active compound to be tested, mixed with the emulsifier PS16, is pipetted into the wells of microtiter plates. After the solvent has evaporated, 200 μl of potato/dextrose medium are added to each well.

Beforehand, a suitable concentration of spores or mycelium of the fungus to be tested was added to the medium.

The resulting concentrations of active compound are 0.1, 1, 10 and 100 ppm. The resulting concentration of the emulsifier is 300 ppm.

The plates are then incubated on a shaker at a temperature of 22° C. for 3-5 days, until sufficient growth can be observed in the untreated control.

Evaluation is carried out photometrically at a wavelength of 620 nm. The dose of active compound which causes a 50% inhibition of fungal growth compared to the untreated control (ED$_{50}$) is calculated from the data measured at different concentrations.

TABLE C

In vitro Test for the ED$_{50}$ determination in microorganisms

| Ex. | Active compound | Microorganisms | ED$_{50}$ |
|---|---|---|---|
| According to EP-A 0 545 099: | | | |
| 3.37 | F$_2$HC-thiazole(CH$_3$)-C(O)NH-phenyl-(4'-F-phenyl) | Rhizoctonia solani<br>Septoria tritici | <100<br>84.24 |
| According to the invention: | | | |
| 3 | F$_2$HC-thiazole(CH$_3$)-C(O)NH-phenyl-(4'-CF$_3$-phenyl) | Rhizoctonia solani<br>Septoria tritici | <0.1<br>0.36 |

TABLE C-continued

In vitro Test for the $ED_{50}$ determination in microorganisms

| Ex. | Active compound | Microorganisms | $ED_{50}$ |
|---|---|---|---|
| 4 | 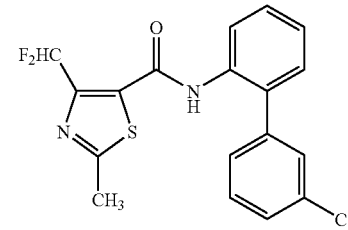 | Rhizoctonia solani<br>Septoria tritici | <0.1<br>0.45 |
| 5 | 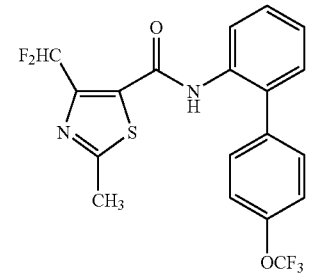 | Rhizoctonia solani<br>Septoria tritici | <0.1<br>0.25 |
| 6 | 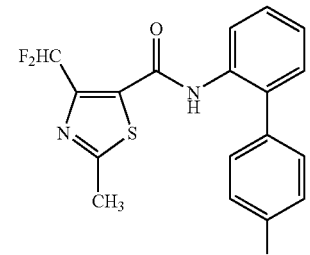 | Rhizoctonia solani<br>Septoria tritici | 3.25<br>3.51 |
| 7 | 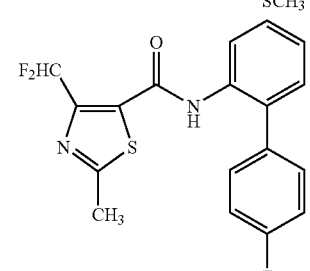 | Rhizoctonia solani<br>Septoria tritici | 0.48<br>0.68 |

What is claimed is:

1. A difluoromethylthiazolylcarboxanilide of formula (I)

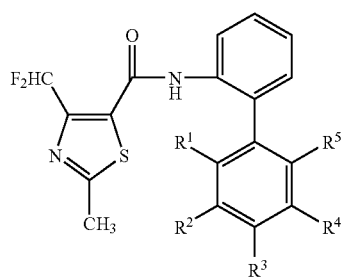

(I)

in which $R^1$, $R^2$, $R^3$, $R^4$, and $R^5$ independently of one another represent hydrogen, halogen, cyano, nitro, $C_1$-$C_6$-alkyl, $C_2$-$C_6$-alkenyl, $C_1$-$C_4$-alkoxy, $C_1$-$C_4$-alkylthio, $C_1$-$C_4$-alkylsulphonyl, or $C_3$-$C_6$-cycloalkyl, or represent $C_1$-$C_4$-haloalkyl, $C_1$-$C_4$-haloalkoxy, $C_1$-$C_4$-haloalkylthio, or $C_1$-$C_4$-haloalkylsulphonyl having in each case 1 to 5 halogen atoms, with the proviso that $R^1$, $R^2$, $R^3$, $R^4$, and $R^5$ do not simultaneously represent hydrogen, or $R^1$ and $R^2$ together or $R^2$ and $R^3$ together optionally also represent optionally halogen- or $C_1$-$C_6$-alkyl-substituted alkenylene.

2. A difluoromethylthiazolylcarboxanilide of formula (I) according to claim 1 in which $R^1$, $R^2$, $R^3$, $R^4$, and $R^5$ independently of one another represent hydrogen, fluorine, chlorine, bromine, cyano, nitro, methyl, ethyl, n- or i-propyl, n-, i-, s-, or t-butyl, methoxy, ethoxy, methylthio, ethylthio, n- or i-propyl thio, cyclopropyl, trifluoro-methyl, trichloromethyl, trifluoroethyl, difluoromethoxy, trifluoromethoxy, difluorochloromethoxy, trifluoroethoxy, difluoromethylthio, difluorochloro-methylthio, or trifluoromethylthio, with the proviso that $R^1$, $R^2$, $R^3$, $R^4$, and $R^5$ do not simultaneously represent hydrogen, or $R^1$ and $R^2$ together or $R^2$ and $R^3$ together optionally also represent optionally fluorine-, chlorine-, bromine-, or methyl-substituted butadienylene.

3. A difluoromethylthiazolylcarboxanilide of formula (I) according to claim 1 in which $R^1$, $R^2$, $R^3$, $R^4$, and $R^5$ independently of one another represent hydrogen, fluorine, chlorine, bromine, methyl, methoxy, methylthio, trifluoromethyl, difluoromethoxy, trifluoromethoxy, difluoromethylthio, or trifluoromethylthio, with the proviso that $R^1$, $R^2$, $R^3$, $R^4$, and $R^5$ do not simultaneously represent hydrogen.

4. A difluoromethylthiazolylcarboxanilide of formula (I) according to claim 1 in which
  $R^1$, $R^2$, $R^4$, and $R^5$ each represent hydrogen, and
  $R^3$ represents halogen, cyano, nitro, $C_1$-$C_6$-alkyl, $C_2$-$C_6$-alkenyl, $C_1$-$C_4$-alkoxy, $C_1$-$C_4$-alkylthio, $C_1$-$C_4$-alkylsulphonyl, or $C_3$-$C_6$-cycloalkyl, or represents $C_1$-$C_4$-haloalkyl, $C_1$-$C_4$-haloalkoxy, $C_1$-$C_4$-haloalkylthio, or $C_1$-$C_4$-haloalkylsulphonyl having in each case 1 to 5 halogen atoms.

5. A difluoromethylthiazolylcarboxanilide of formula (I) according to claim 1 in which
  $R^1$, $R^2$, $R^4$, and $R^5$ each represent hydrogen, and
  $R^3$ represents fluorine, chlorine, bromine, methyl, trifluoromethyl, trifluoro-methoxy, or trifluoromethylthio.

6. A difluoromethylthiazolylcarboxanilide of formula (I) according to claim 1 in which
  $R^2$, $R^4$, and $R^5$ each represent hydrogen, and
  $R^1$ and $R^3$ independently of one another represent halogen, cyano, nitro, $C_1$-$C_6$-alkyl, $C_2$-$C_6$-alkenyl, $C_1$-$C_4$-alkoxy, $C_1$-$C_4$-alkylthio, $C_1$-$C_4$-alkylsulphonyl, or $C_3$-$C_6$-cycloalkyl, or represent $C_1$-$C_4$-haloalkyl, $C_1$-$C_4$-haloalkoxy, $C_1$-$C_4$-haloalkylthio, or $C_1$-$C_4$-haloalkylsulphonyl having in each case 1 to 5 halogen atoms.

7. A difluoromethylthiazolylcarboxanilide of formula (I) according to claim 1 in which
  $R^2$, $R^4$, and $R^5$ each represent hydrogen, and
  $R^1$ and $R^3$ independently of one another represent fluorine, chlorine, bromine, methyl, or trifluoromethyl.

8. A difluoromethylthiazolylcarboxanilide of formula (I) according to claim 1 in which
  $R^1$, $R^4$, and $R^5$, each represent hydrogen, and
  $R^2$ and $R^3$ independently of one another represent halogen, cyano, nitro, $C_1$-$C_6$-alkyl, $C_2$-$C_6$-alkenyl, $C_1$-$C_4$-alkoxy, $C_1$-$C_4$-alkylthio, $C_1$-$C_4$-alkylsulphonyl, or $C_3$-$C_6$-cycloalkyl, or represent $C_1$-$C_4$-haloalkyl, $C_1$-$C_4$-haloalkoxy, $C_1$-$C_4$-haloalkylthio, or $C_1$-$C_4$-haloalkylsulphonyl having in each case 1 to 5 halogen atoms.

9. A difluoromethylthiazolylcarboxanilide of formula (I) according to claim 1 in which
  $R^1$, $R^4$, and $R^5$ each represent hydrogen, and
  $R^2$ and $R^3$ independently of one another represent fluorine, chlorine, bromine, methyl, or trifluoromethyl.

10. A difluoromethylthiazolylcarboxanilide of formula (I) according to claim 1 in which
  $R^1$, $R^3$, and $R^5$ each represent hydrogen, and
  $R^2$ and $R^4$ independently of one another represent halogen, cyano, nitro, $C_1$-$C_6$-alkyl, $C_2$-$C_6$-alkenyl, $C_1$-$C_4$-alkoxy, $C_1$-$C_4$-alkylthio, $C_1$-$C_4$-alkylsulphonyl, or $C_3$-$C_6$-cycloalkyl, or represent $C_1$-$C_4$-haloalkyl, $C_1$-$C_4$-haloalkoxy, $C_1$-$C_4$-haloalkylthio, or $C_1$-$C_4$-haloalkylsulphonyl having in each case 1 to 5 halogen atoms.

11. A difluoromethylthiazolylcarboxanilide of formula (I) according to claim 1 in which
  $R^1$, $R^3$, and $R^5$ each represent hydrogen, and
  $R^2$ and $R^4$ independently of one another represent fluorine, chlorine, bromine, methyl, or trifluoromethyl.

12. A difluoromethylthiazolylcarboxanilide of formula (I) according to claim 1 in which $R^5$ represents hydrogen.

13. A composition for controlling unwanted microorganisms comprising one or more thiazolylcarboxanilides of formula (I) according to claim 1 and one or more extenders and/or surfactants.

* * * * *